United States Patent [19]

Sinclair et al.

[11] Patent Number: 4,800,066
[45] Date of Patent: Jan. 24, 1989

[54] END OF LIFE INDICATOR FOR AUTOMATIC TOILET CLEANING DEVICES

[75] Inventors: Richard G. Sinclair; Sylvester Sowell, both of Columbus, Ohio

[73] Assignee: The Drackett Company, Cincinnati, Ohio

[21] Appl. No.: 887,751

[22] Filed: Jul. 21, 1986

[51] Int. Cl.[4] .......................................... G01N 31/22
[52] U.S. Cl. ..................................... 422/55; 422/58; 422/119
[58] Field of Search .......................... 422/55, 58, 119; 428/402; 73/61.1 R; 436/163

[56] References Cited

U.S. PATENT DOCUMENTS

| 2,449,274 | 9/1948 | Broll | 424/7.1 |
|---|---|---|---|
| 2,451,022 | 10/1948 | Dohrmann | 424/7.1 |
| 3,504,384 | 4/1970 | Radley et al. | 4/228 |
| 3,607,103 | 9/1971 | Kiefer | 422/119 |
| 3,853,478 | 12/1974 | Rodgers | 422/119 |
| 3,860,394 | 1/1975 | Tepas, Jr. et al. | 422/119 |
| 3,867,101 | 2/1975 | Herring | 422/119 |
| 3,942,467 | 3/1976 | Witonsky | 422/119 X |
| 4,046,507 | 9/1977 | Zweifel et al. | 8/526 |
| 4,062,649 | 12/1977 | Kuderna et al. | 422/119 X |
| 4,180,064 | 12/1979 | Heller et al. | 71/1 X |
| 4,229,410 | 10/1980 | Kosti | 422/28 |
| 4,248,597 | 2/1981 | McNeely | 422/58 X |
| 4,435,857 | 3/1984 | Meloy | 4/228 |
| 4,450,594 | 5/1984 | Hotchkin | 4/228 |
| 4,460,490 | 7/1984 | Barford et al. | 252/92 |

FOREIGN PATENT DOCUMENTS 0184888 6/1986 European Pat. Off. .

Primary Examiner—Barry S. Richman
Assistant Examiner—Jill Johnston
Attorney, Agent, or Firm—Charles J. Zeller

[57] ABSTRACT

An end of life indicator for use in a toilet cistern with an ambient solution containing an active disinfectant component. The end of life indicator comprises a core of water soluble dyestuff surrounded by a polymer resistant to bleaching by said disinfectant solution. Upon the depletion of the active disinfectant component surrounding the end of life indicator, the alkalinity of the solution increases to a predetermined level whereupon hydrolysis of the polymer coating continues until water penetrates or dissolves the coating sufficiently to come into contact with the water soluble dye.

8 Claims, 1 Drawing Sheet

END OF LIFE INDICATOR FOR AUTOMATIC TOILET CLEANING DEVICES

BACKGROUND OF THE INVENTION

1. Field of the Invention

This invention relates to devices for automatically cleaning toilets. More particularly, the invention relates to means for indicating the end of useful life of the active cleansing and/or disinfectant compound used in automatic toilet cleaning devices.

2. Description of the Prior Art

Automatic (self-operating) toilet cleaners adapted for placement in the tank or cistern of a toilet are well known and generally comprise a container within which is provided a disinfectant and/or detergent composition. The container empties and refills on the occasion of a flush, and during the quiescent period between two flushes a minor amount of the disinfectant and/or detergent composition is dissolved within the container to form a suitably concentrated, typically essentially saturated, solution thereof. The essentially saturated solution is released from the container on the next flush, the essentially saturated solution being substantially diluted with tank water and then delivered at a suitable and effective cleaning/disinfecting level to the bowl.

Since the cleaning devices are often not visible and the disinfectant and detergent compositions are often colorless, there is considerable difficulty in determining when the disinfectant and/or detergent composition in the cleaning device has been depleted to the point where it is no longer effective. There is an obvious need to have some means of indicating the expiration of the useful life of such automatic toilet cleaners. Several end of life indicators have been developed. Use of a water-soluble dye as an indicator, however is not an easy solution to this problem as the essentially sautrated solutions bleach the active dye chromophores. Such prior art end of life indicators may be divided into two categories.

The first category comprises those devices using dyestuffs which are kept segregated from the water in the cistern until the active bleaching components in the water have been depleted to a predetermined level. This category of devices is represented, for example, by U.S. Pat. Nos. 4,450,594 and 3,867,101. In a non-toilet environment, a similar end of life indicator is disclosed in U.S. Pat. No. 2,451,022. U.S. Pat. No. 4,450,594 discloses a tank dispenser having a chlorine based tablet resting upon an inverted cup shaped member containing a water soluble dye. When the chlorine tablet is dissolved below a predetermined weight, the inverted cup shaped member is automatically released, thus permitting water to come into contact with the dye to create the end of life indication. In U.S. Pat. No. 3,867,101 a water soluble dye tablet is placed in the bottom of a dispenser and is totally covered with a water soluble material composition of detergent and/or disinfectant. When the detergent and/or disinfectant has been depleted to a predetermined point, the water will come into contact with the dyestuff and create the end of life indication. In U.S. Pat. No. 2,451,022 a dyestuff is contained in a core enclosed within a shell. The shell coating is shellac mixed with powdered magnesium carbonate and designed to disintegrate in a predetermined length of time in an antiseptic and germicidal solution. After the predetermined length of time, the shellac coating will be worn away and the end of life indication will occur well before the antiseptic and germicidal solution is completely exhausted.

The second category of end of life indicators comprises devices using dyestuffs admixed to disinfectant and/or detergent compositions so that the dyesuff is continuously being dissolved in the surrounding solution. Examples of devices in this second category are shown in U.S. Pat. Nos. 4,435,857, 4,229,410, 4,460,490 and 3,504,384. In a non-toilet environment, another example of an end of life indicator is shown in U.S. Pat. No. 2,449,274. In all of the devices of the second category, the colored dyestuff is continuously in contact with the surrounding water and the color is either visible or suppressed (although in the '410 patent the water is only in contact with the dyestuff during actual flushing of the toilet). The end of life indication occurs when either the dye color disappears (as in U.S. Pat. Nos. 4,229,410 and 3,504,384) or when the amount of bleach in the solution has been depleted to the point where it is insufficient to bleach the dye thereby allowing the dye color to appear (as in U.S. Pat. Nos. 4,435,857 and 4,460,490). In U.S. Pat. No. 2,449,274 the end of life indication occurs when the phenol coefficient of the composition has been reduced to a predetermined value by contamination thereby enabling the dye color to become visible.

Each of the categories of end of life indicators has certain deficiencies. The first category of end of life indicators cited above is costly to manufacture because of the need to protect the dye from premature contact with water. Additionally, those end of life indicators which are similar to that shown in U.S. Pat. No. 2,451,022 which are timed irrespective of the concentration of the active ingredient in the ambient solution may provide erroneous indications of the end of life of the active component. The second category of end of life indicators are inefficient since they require excessive amounts of dyestuffs to be utilized.

Accordingly, there is needed an end of life indicator capable of being placed in a solution and remaining in the solution until the concentration of active ingredients falls to a predetermined level and only then providing an end of life indication. It is, therefore, an object of this invention to provide a means for positively sensing the decrease in the active bleach component remaining in solution in a toilet cistern and only then enabling water to come into contact with a water soluble dye. It is a further object of this invention to provide a water soluble dye encapsulated in a bleach-impervious coating. It is yet another object of this invention to provide an end of life indicator which protects a dye from being bleached by ambient solution while enabling the dye color to be released into the ambient solution at a predetermined level of alkalinity.

SUMMARY OF THE INVENTION

These and other objects of the invention are achieved by the embodiments disclosed herein which provide for an end of life indicator for an aqueous solution containing an active detergent or disinfectant component, comprising: a core composition of a water soluble dye, said dye being one which is bleachable by said solution, and a coating of a polymer that is substantially resistant to said solution that surrounds the end of life indicator, the coating being hydrolyzable by water when the concentration of active detergent or disinfectant component in the solution is at or below a predetermined level. In one embodiment, the water soluble dye is coated with a composition of polymethylmethacrylate from a methylene chloride solution. In another embodiment, this coating composition is admixed with a predetermined concentration of styrene and acrylic acid copolymer. In order to adjust the point at which the end of life indication occurs, the proportions of the various compositions in the coating may be varied. In general, the coating of the water soluble dye is chosen to be a polymer, the hydrolysis of which increases as the pH of the surrounding, i.e., ambient, solution increases.

BRIEF DESCRIPTION OF THE DRAWING

The drawing illustrates a toilet dispenser which uses a preferred embodiment of the present invention.

DESCRIPTION OF THE PREFERRED EMBODIMENT

Figure 1:
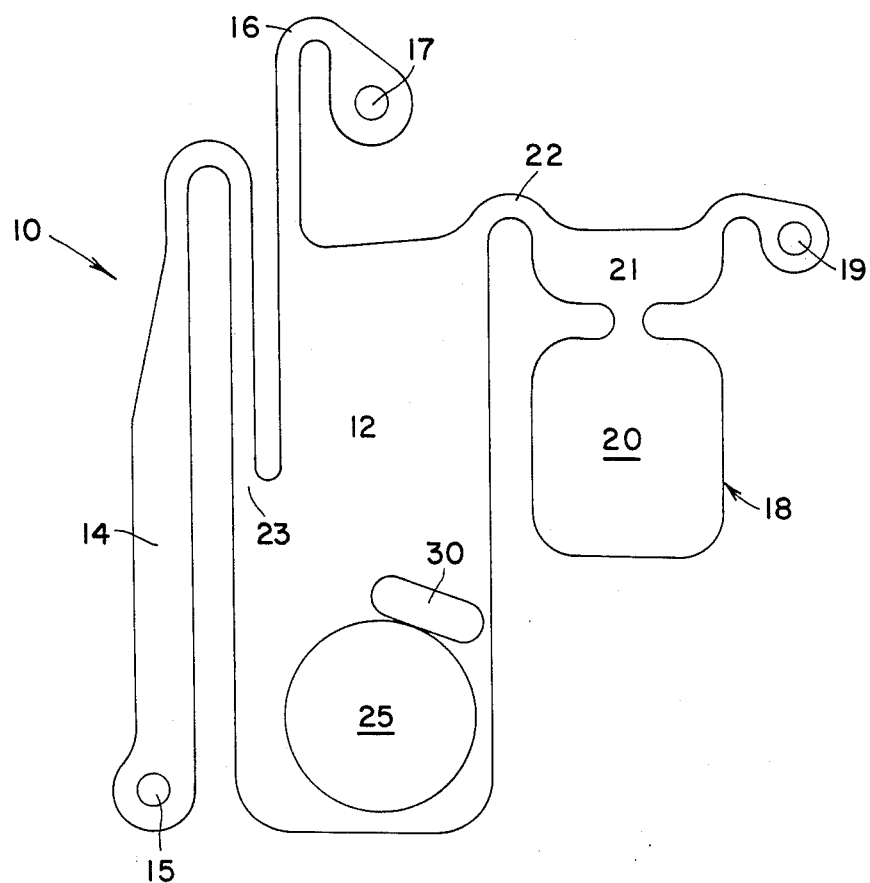

Referring to the drawing, there is shown one type of a toilet dispenser for utilizing a preferred embodiment of the end of life indicator which is the subject of this invention. The dispenser 10 contains in its main compartment 12 a water dissolvable tablet 25 of a disinfectant composition and an end of life indicator tablet 30 prepared in accordance with the principles of this invention. The disinfectant is one which provides an acid pH in aqueous solution. Trichloroisocyanuric acid is the preferred disinfectant.

The dispenser 10 also includes an inlet/discharge conduit 14 having discharge opening 15; a vent conduit 16 having vent opening 17, and optionally dispensing means 18 to permit a small amount of an alkalinity agent solution to enter the main compartment 12, the purpose for which is hereinafter described, the dispensing means 18 shown in FIG. 1 having an inlet opening 19, a compartment 20 for containing the alkalinity agent, an alkalinity solution reservoir 21, and alklinity solution transfer conduit 22. It is seen that the conduit 14 enters the main compartment 12 at 23, a predetermined distance above the bottom of the device 10. Accordingly, after a flush the compartment 12 remains filled with essentially saturated disinfectant up to the level 23, and refill of the compartment 12 with water does not so dilute the residual solution as to raise its pH to a point where substantial hydrolysis of the disinfectant resistant coating would occur after repeated uses. During the quiescent period between flushes, the solution concentration will gradually increase with time by dissolution of the active, until equilibrium is achieved.

It is noted that one advantage of the invention is that the construction of the dispenser is simplified in that all components other than the indicator tablet 30 are conventional. Another advantage is that dispenser manufacturing cost is decreased since care need not be taken to protect tablet 30 from contact with the water.

While indicator tablet 30 is termed a "tablet", it will be understood by those of ordinary skill in the art that this term does not limit the invention to items produced on a tablet press. This invention is intended to cover the product of any suitable method of production which results in a water soluble dye that is subject to bleaching by a disinfectant solution, the water soluble dye being encased in a disinfectant solution impervious coating.

Tablet 30 contains a core of any water soluble dye. Except as noted, the dye core in the examples disclosed below was Hidacid Aqua Blue NSCR (containing as the primary chromophore Colour Index Dye No. 52,035) (from Hilton-Davis, Cincinnati, Ohio) enclosed within a No. 1 gelatin capsule (from Eli Lilly and Co., Indianapolis, Ind.). The dye need not be enclosed in gelatin capsules in order to achieve the advantages of this invention, however, in the manufacturing process employed to produce the disclosed examples it was found convenient to use this form.

Tablet 30 further comprises a coating surrounding the water soluble core in order to protect it from premature contact with the surrounding water. The coating on tablet 30 should be relatively uniform and free of holes, dimples, etc. Defects in the coating may allow premature water penetration and consequent dye release. The coating must obviously be resistant to the disinfectant solution while sensitive to neutral or alkaline tap water. The examples below are based on the use of saturated or nearly saturated solutions of trichloroisocyanuric acid (TCICA). However, any cleaning or disinfectant solution is suitable that has an acid pH, preferably in the range of from about 2.5 to about 5.5.

The coating may be selected from among those materials having a certain degree of inertness to trichloroisocyanuric acid. The coating is characterized by having a molecular weight sufficient to obtain integrated, well-formed impact resistant films, typically above about 50,000. Various combinations of materials were used to produce different coatings and the results were tabulated to show how long the resulting tablets lasted in a saturated or nearly saturated solutions of TCICA, pH 8 buffer, pH 10 buffer and tap water. Referring to Table 1, the indicator tablets were prepared by hand-dipping dye-filled gelatin capsules into a resin-containing solution. Except as noted, the solvent was methylene chloride. Although not critical, the resin concentration should not be so high as to prevent it from being dissolved in the solvent or raise the solution viscosity to unworkable levels. It should not be so low as to require an excessive number of immersions for the capsule to acquire the requisite coating. A resin concentration of between about 10 to 30% by weight is preferred. No specific attention was given to coating thickness other than to assure relatively uniform thickness among the various examples. Each sample was placed in a vial (and agitated occasionally) containing the specified ambient solution.

A desired goal of the present invention, as illustrated by the examples, is to prevent release of the dye over a reasonable period of time in the presence of an ambient solution having an essentially saturated concentration of disinfectant. A conventional toilet dispenser might have an average useful life of 15-30 days, and it is desirable to make the coating impervious to bleach for at least the same time period. It will be noted that the examples listed in Table 1 were hand-dipped and those having 90%-100% polymethyl methacrylate (PMMA) coating provided the best resistance to bleaching while simultaneously being hydrolyzable in tap water in a short amount of time. In some of the examples, the coating was a composition of PMMA and XC-4011 (a copolymer of styrene and acrylic acid in a 85/15 ratio, from American Cyanamid).

TABLE 1

RELEASE TIMES FOR ENCAPSULATED DYE[a]

| Coating (Composition in Wt. %, Components) | Time Before Color Release in Various Media | | | |
|---|---|---|---|---|
| | TCICA Solution | pH 8 Buffer | pH 10 Buffer | Tap Water |
| None | <1 hr | <1 hr | <1 hr | — |
| Ethylene-maleic acid derivative | <1 day | <1 day | <1 day | — |
| Polystyrene | <1 day | <1 day | <1 day | — |
| Polylactic acid | >12 days | 12 days | <1 day | — |
| 50/50, XC-4011 polystyrene | <1 hr | — | — | — |
| Ethylene-acrylic (15% AA)[b] | <1 hr | <1 hr | <1 hr | — |
| PMMA | 10 days | <1 hr | <1 hr | — |
| 90/10, | 14 days | 3 days | <3 days | 3 days |
| PMMA/XC-4011 | | | | |
| 75/25, PMMA/XC-4011 | 7 days | <3 days | <3 days | — |
| 50/50, PMMA/XC-4011 | 4 days | <3 days | <3 days | — |
| 0/100, PMMA/XC-4011 | <1 hr | <1 hr | <1 hr | — |
| 100/0, PMMA/XC-4011 | 20 days | 1 day | 14 days | 1 day |

[a]Number 1 gelatin capsules containing Hidacid Aqua Blue Dye with coating applied by hand-dipping.
[b]Number 1 gelatin capsules containing Pylam Intralite Turquoise 8GL dye. Coating applied by hand-dipping into toluene-resin solution.

While some of the examples of Table 1 are suitable for the intended purpose, there are considerations which make it preferable to provide coatings of different compositions to facilitate automated production of the indicator tablets. Accordingly, samples of indicator tablets were prepared using a fluidized bed coating process and the samples were similarly placed in vials. The results are tabulated in Table 2. The coating thicknesses were varied to determine the significance of the thickness for various coating blends. In the preparation of the indicator tablets by the fluidized bed technique, it was found that the proper chemical resistance to the disinfectant solution is imparted, as shown in Table 3, by a coating formed of: a blend of polymethyl methacrylate, a copolymer of methyl methacrylate and butyl methacrylate, and a copolymer of styrene and acrylic acid. The first polymer, polymethyl methacrylate, provides bleach resistance and prevents tackiness in the coating. The second polymer, the butyl copolymer, adds much resistance to the bleaching effort of the TCICA and a great deal of toughness. The third polymer, the acrylic copolymer, adds the selective degradative reaction with alkaline tap water.

The blend of polymers was deemed desirable because, while PMMA alone would achieve the advantages of the invention, PMMA is quite brittle and prone to crazing in thin coatings. Thus, repeatability and durability of indicator tablets using primarily PMMA cannot be assured, as shown in Table 2. As also shown in Table 2, replacing PMMA with the butyl methacrylate copolymer produced too much resistance to tap water.

TABLE 2

RELEASE TIMES FOR ENCAPSULATED DYE[a]

| Coating (Composition in Wt. %, Components) | Coating Thickness, Microns | Time Before Color Release in Various Media | | | |
|---|---|---|---|---|---|
| | | TCICA Solution | pH 8 Buffer | pH 10 Buffer | Tap Water |
| 90/10, PMMA/XC-4011 | — | <1 day–2 days | — | — | <1 day–2 days |
| 90/10, PMMA/XC-4011 from toluene, CH$_2$Cl$_2$ | 150 | <1 day | — | — | <1 day |
| 90/10, PMMA/XC-4011 from toluene, CH$_2$Cl$_2$ | 65 | <1 day | — | — | <1 day |
| 90/10, butyl & methyl methacrylate copolymer/XC-4011 | 227 | >44 days | — | — | >44 days |
| 90/10, butyl & methyl methacrylate copolymer/XC-4011 | 123 | >44 days | — | — | 4 days v. slight |
| 75/25, butyl & methyl methacrylate copolymer/XC-4011 | 85 | >28 days | >20 days | 15–18 days | >28 days |
| 75/25, butyl & methyl methacrylate copolymer/XC-4011 | 150 | >28 days | >20 days | 11 days | >28 days |
| 75/25, butyl & methyl methacrylate copolymer/XC-4011 | 238 | >28 days | >20 days | 19 days | >28 days |

[a]Number 1 gelatin capsules containing .38–.40 grams Hidacid Aqua Blue dye, and coated in fluidized bed.

In Table 3 the PMMA was blended with a first copolymer of methyl methacrylate and butyl methacrylate (approximately a 60/40 weight ratio copolymer, Rohm and Haas, Acryloid Resin B-66) and a second copolymer of styrene and acrylic acid (85/15 weight ratio, styrene to acrylic acid, American Cyanamid XC-4011). The first copolymer provides resistance to the disinfectant solution and crazing and the second copolymer promotes the alkaline sensitivity of the coating. It can be seen that coating blends of PMMA, butyl methacrylate (B-66) copolymer and XC-4011 produce desirable coatings if the proper balance of the constituent materials is utilized. As shown in Table 3, the 50/25/25 and the 80/10/10 blends of PMMA/B-66/XC-4011 were all too brittle as reflected in the early color release. It was discovered that thin cast films of these blends become fragile at approximately 30% or less of B-66. At this level the films withstand impact and just begin to fold before snapping.

Increasing the amount of butyl copolymer increased both the release time and the impact resistance. A 50/40/10 composition was observed to have excellent coating characteristics and was impact resistant, however, it did not exhibit much difference in its release times in tap water versus disinfectant solution. Release times for this sample were more dependent on the amount of coating rather than the ambient solutions.

TABLE 3

RELEASE TIMES FOR ENCAPSULATED DYE[a]

| Composition[b] | Coating Weight Percent of Indicator | Thickness, Microns | Time Before Color Release Tap Water[c] | Disinfectant Solution[d] |
|---|---|---|---|---|
| 50/25/25, PMMA/B-66/XC-4011 | 5.48 | — | <2 hrs | 1–2 days |
| 50/25/25, PMMA/B-66/XC-4011 | 9.06 | — | <1 day | 2–5 days |
| 50/25/25, PMMA/B-66/XC-4011 | 12.53 | — | 1–2 days | 5–>5 day |
| 50/25/25, PMMA/B-66/XC-4011 | 15.01 | — | >5 days | >5 days |
| 80/10/10, PMMA/B-66/XC-4011 | 0.54 | — | <1 hr[e] | <1 hr[e] |
| 80/10/10, PMMA/B-66/XC-4011 | 1.15 | — | <1 hr[e] | <1 hr[e] |
| 80/10/10, PMMA/B-66/XC-4011 | 3.43 | — | <1 hr[e] | <1 hr[e] |
| 80/10/10, PMMA/B-66/XC-4011 | 4.61 | 80 | <1 hr[e] | <1 hr[e] |
| 50/40/10, PMMA/B-66/XC-4011 | 4.12 | — | 1–5 days | 1–5 days |
| 50/40/10, PMMA/B-66/XC-4011 | 6.84 | — | 1–3 days | 1–3 days |
| 50/40/10, PMMA/B-66/XC-4011 | 9.48 | — | 5–35 days | 7–36 days |
| 50/40/10, PMMA/B-66/XC-4011 | 11.1 | 101 | 13–35 days | 9–14 days |
| 50/30/20, PMMA/B-66/XC-4011 | 5.6 | 44 | 2–4 days | 1–6 days |
| 50/30/20, PMMA/B-66/XC-4011 | 10.2 | 83 | 5–72 hours | 15 days |
| 50/30/20, PMMA/B-66/XC-4011 | 16.8 | 139 | 6–8 days | >30 days |
| 50/30/20, PMMA/B-66/XC-4011 | 23.0 | 192 | >30 days | >30 days |
| 40/40/20, PMMA/B-66/XC-4011 | 6.5 | 57 | 5 hrs, 3 days, 7 days | 13 days |
| 40/40/20, PMMA/B-66/XC-4011 | 11.9 | 102 | >30 days | >30 days |
| 40/40/20, PMMA/B-66/XC-4011 | 16.8 | 146 | >30 days | >30 days |
| 40/40/20, PMMA/B-66/XC-4011 | 22.3 | 195 | >30 days | >30 days |
| 50/30/20, PMMA/B-66/XC-4011 | — | 145 | 6–8 days | >30 days |
| 50/30/20 | 13.1 | 112 | 2–4 hrs[e]; 4–7 days | <24 hrs[e] >18 days |
| 45/30/25 | 18.1 | 167 | 3–7 days | <24 hrs[3] 10–18 days >18 days |

[a]No. 1 gelatin capsules containing 0.38–0.40 grams of Hidacid Blue dye and coated in fluidized bed.
[b]Polymer blend at the indicated weight ratio.
PMMA = polymethyl methacrylate
B-66 = copolymer of methyl methacrylate and butyl methacrylate, approximately 60/40 ratio, respectively
XC-4011 = copolymer of styrene and acrylic acid, approximately 85/15 ratio, respectively
[c]Capsule in static test vial; pH = 7.9 (initial), 6.6 (after 36 days)
[d]Capsule in static test vial of saturated TCICA solution (pH = 2.9–2.3)
[e]Coatings exhibited failure from septal defects.

In general, the following conclusions may be derived from Table 3 about the required coating characteristics:

1. The coatings must be greater than 25% butyl methacrylate copolymer to have adequate toughness.
2. The coatings must be less than 40% butyl methacrylate to obtain sensitivity to tap water.
3. Reproducible results are obtained at coating thicknesses of approximately 100 to 150 microns (4 to 6 mil).
4. A 10–25% content of the acrylic acid-styrene copolymer can impart the required chemical sensitivity to tap water.

Of the examples disclosed the optimized ratio of PMMA/butyl methacrylate copolymer/acrylic acid copolymer is between 50/30/20 and 45/30/25.

Because of acidic tap water in some locales, it is desirable to use a dispenser which would permit a small amount of an alkalinity agent (such as sodium bicarbonate) to enter the main compartment 12 of the dispenser. In the dispenser shown in FIG. 1, a compartment 20 containing the alkalinity agent is provided to dispense from a reservoir 21 an alkaline solution into the main compartment of the dispenser on each flush. The amount of such alkalinity agent added during each dispenser refill is low and does not materially affect the pH of the disinfectant solution. The alkalinity agent reacts with a minor amount of disinfectant to generate carbon dioxide, which fills U-shaped conduit 22, thereby isolating the reservoir 21 from the main compartment 12 during the period between flushes. When the disinfectant tablet 25 is exhausted, the alkalinity agent will raise the pH of the acidic tap water then contained in the compartment 12 to a suitable value, typically neutral or alkaline, at which hydrolysis of the coating will commence.

The blend of polymers described above is only one example of the invention. Other blends are also possible to achieve the functional characteristics of disinfectant inertness and toughness, slight water penetrability and alkaline hydrolyzability. Such other suitable materials are listed in Table 4.

TABLE 4

| A<br>Bleach<br>Inertness and Toughness | B<br>Slight-Water Penetrability | C<br>Alkaline Hydrolyzable |
| --- | --- | --- |
| (1) methyl methacrylate-butyl methacrylate copolymer | (1) Polymethyl methacrylate | (1) Ethylene vinyl acetate copolymer |
| (2) SBR (low styrene) | (2) Polystyrene | (2) Ethylene maleic anhydride copolymer |
| (3) PVC | (3) SBR (high styrene) | (3) Ethylene methacrylic acid copolymer |
| (4) PVC-vinylidene chloride copolymer | | (4) Polyvinylchloride-vinyl acetate copolymer |
| (5) Polyethylene | | (5) Polyvinyl acetate/polyvinyl acetate-vinyl alcohol (partially hydrolyzed polyvinylacetate) |
| | | (6) Styrene-maleic anhydride copolymer |

It will be obvious to those of ordinary skill in the art that numerous improvements and modifications may be made to the preferred embodiment of the invention disclosed herein without departing from the spirit and scope thereof.

What is claimed is:

1. An end of life indicator for an aqueous solution containing an active component, and having a pH less than a predetermined value, comprising:
   a core of water soluble dye, and
   a coating completely surrounding said core, said coating being a polymer composition substantially resistant to an aqueous solution and hydrolyzable when the end of life indicator is within an aqueous media having a pH above a predetermined value, exhaustion of an active component being indicated by release of said dye upon hydrolysis of said coating.

2. An end-of-life indicator according to claim 1 wherein the resistance of the coating to hydrolysis decreases as the pH of the solution increases.

3. An end of life indicator according to claim 1 wherein said coating comprises a composition of polymethyl methacrylate, a first copolymr of methyl methacrylate and butyl methacrylate, and a second copolymer of styrene and acrylic acid, said first copolymer comprising 25% to 40% by weight of said composition and said second copolymer comprising 10% to 25% by weight of said composition.

4. An end of life indicator according to claim 3 wherein said coating has a thickness in the range of 100 to 150 microns.

5. An end-of-life indicator according to claims 1, 3, or 4 wherein the coating is substantially resistant to an acidic, aqueous solution containing a disinfectant active component, the coating being hydrolyzable when the end-of-life indicator is within an aqueous media having an alkaline pH.

6. An end of life indicator according to claim 5 further comprising means for adding an alkalinity agent to said solution to ensure release of said water soluble dye when said active disinfectant component is exhausted.

7. An end of life indicator according to claim 3 or 4 wherein the weight ratio of methyl methacrylate to butyl methacrylate in the first copolymer is about 60/40 and wherein the weight ratio of styrene to acrylic acid in the second copolymer is about 85/15.

8. A end-of-life indicator according to claim 7 wherein the coating is substantially resistant to an aqueous solution containing trichloroisocyanuric acid as a disinfectant, the aqueous solution having a pH in the range of from about 2.5 to about 5.5.

* * * * *